United States Patent
Takeuchi et al.

(10) Patent No.: US 6,245,734 B1
(45) Date of Patent: Jun. 12, 2001

(54) PHYSIOLOGICALLY ACTIVE POLYOXYPEPTIN AND DEOXYPOLYOXYPEPTIN AND ANTICANCER DRUGS CONTAINING THE SAME

(75) Inventors: Tomio Takeuchi; Kazuo Umezawa; Shinichi Kondo; Yoko Ikeda; Hiroshi Naganawa, all of Tokyo; Masa Hamada, Naito-machi, all of (JP)

(73) Assignee: Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 09/445,581
(22) PCT Filed: Jun. 12, 1998
(86) PCT No.: PCT/JP98/02599
§ 371 Date: Dec. 13, 1999
§ 102(e) Date: Dec. 13, 1999
(87) PCT Pub. No.: WO98/56809
PCT Pub. Date: Dec. 17, 1998

(30) Foreign Application Priority Data

Jun. 13, 1997 (JP) .................................................. 9-156649
Sep. 19, 1997 (JP) .................................................. 9-255084

(51) Int. Cl.[7] .......................... A01N 61/00; A01N 43/00; A01N 43/58; A01N 43/64; A61K 31/535
(52) U.S. Cl. .............................. 514/1; 514/183; 514/247; 514/359; 514/228.8
(58) Field of Search ................................. 514/1, 183, 247, 514/359, 228.8

Primary Examiner—Jezia Riley
(74) Attorney, Agent, or Firm—Larson & Taylor PLC (57) ABSTRACT

As novel substances having an activity of inducing an apoptosis even on the apoptosis-resistant cancer cells, there are obtained polyoxypeptin and deoxypolyoxypeptin represented by the following general formula (I)

(I)

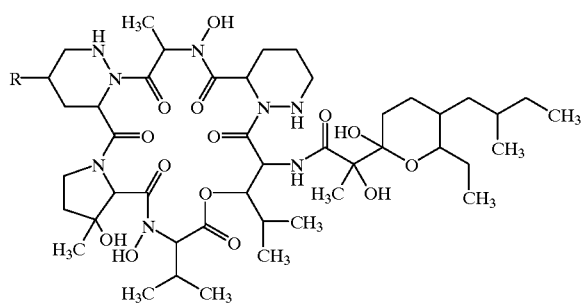

wherein R denotes a hydroxyl group for polyoxypeptin, or R denotes a hydrogen atom for deoxypolyoxypeptin, by cultivation of Streptomyces sp. MK498-98F14 strain. Polyoxypeptin and deoxypolyoxypeptin are physiologically active substances which have an activity of inducing apoptosis on a human pancreatic adenocarcinoma cell, AsPC-1 cell.

8 Claims, 8 Drawing Sheets

PHYSIOLOGICALLY ACTIVE POLYOXYPEPTIN AND DEOXYPOLYOXYPEPTIN AND ANTICANCER DRUGS CONTAINING THE SAME

TECHNICAL FIELD

This invention relates to novel physiologically active substances, polyoxypeptin and deoxypolyoxypeptin, which have each an anti-cancer activity and an antibacterial activity against gram-positive bacteria. Polyoxypeptin and deoxypolyoxypeptin according to this invention are physiologically active substances which have an activity of inducing apoptosis not only on such human pancreatic adenocarcinoma cells of a type susceptible to apoptosis and capable of causing apoptosis by treatment with an anti-cancer drug, but also have an activity of inducing apoptosis on such human pancreatic adenocarcinoma cells of a type resistant to apoptosis even upon the treatment with the anti-cancer drug, for example, on AsPC-1 cell, whereby polyoxypeptin and deoxypolyoxypeptin possess anti-cancer or anti-tumor activities. This invention also relates to a process for the production of polyoxypeptin and/or deoxypolyoxypeptin. This invention further relates to an anti-tumor or anti-cancer composition containing polyoxypeptin or deoxypolyoxypeptin as active ingredient. Further, this invention embraces, as a novel microorganism, Streptomyces sp. MK498-98F14 strain which has a characteristic nature capable of producing the physiologically active substances above-mentioned.

BACKGROUND ART

Apoptosis is such a schemed death of cells, of which a particular feature is an immediate death of cells. In 1970's, apoptosis was reported as a new conception for the death of cells [see "Int. Rev. Cytol.", 68, 251(1980)]. As compared with a necrosis which was an old conception for the death of cells already known in the art, apoptosis is characterized in that the period of time lapsed between the time of impartment of a stimulus of causing the death of cells by apoptosis and the time of occurrence of the death of cells by apoptosis is shorter than that for the necrosis, and also that apoptosis does involve no inflammation in the peripheral tissues of the cancer region, and so on. Afterwards, there have been reported that many anti-cancer drugs such as adriamycin and cisplatin have the activities of inducing the apoptosis on some of incubated cancer cells ["Cancer Res.", 53, 1845 (1993) and "Exp. Cell Res.", 211, 231 (1994)].

However, it has become clear now that adriamycin or cisplatin as the anti-cancer drug can have an activity of inducing the apoptosis of cells on the leukemia cells and on the experimental cancer cells which were artificially generated by carcinogen virus and the like, but that adriamycin or cisplatin does not induce apoptosis on many of the spontaneously generated human solid cancer cells [see "Rinsho Igaku", 21, No.9, 42–45 (1995)]. That is to say, there exist such human solid cancer cells which possess such property of not inducing the apoptosis by the anti-cancer drugs known and utilized in the art, and which are of the apoptosis-resistant type.

An human pancreatic adenocarcinoma cell, AsPC-1 cell, is a cancer cell described in "In Vitro", 18, 24 (1982)", and AsPC-1 cell exhibits a very strong apoptosis-resistance against such anti-cancer drugs as adriamycin, etc. While, another human pancreatic adenocarcinoma cell, BxPC-3 cell [described in "Cancer Investigation", 4, 15 (1986)], is susceptible to apoptosis. For example, it is already known that adriamycin can induce apoptosis on BxPC-3 cell within 24 hours from the start of treatment with adriamycin at the concentration of 3 $\mu$g/ml, but adriamycin does not induce apoptosis on AsPC-1 cell even at the concentration of 30 $\mu$g/ml of adriamycin.

In the past, nothing was known about such investigations which seek for the drugs capable of inducing the apoptosis on the apoptosis-resistant cancer cells such as the human pancreatic adenocarcinoma cell, AsPC-1 cell. In the clinical applications of conventional anti-cancer drugs of the type which can exhibit a cytotoxicity against cancer cells, it is considered that the "in vivo" contact time between the conventional anti-cancer drug and the cancer cells is a limited one. Thus, it is deducible that a more effective agent would be such an anti-cancer drug which is capable of inducing the apoptosis of cancer cells and thereby capable of making the cell death to be caused on the cancer cells in a shorter time than the conventional anti-cancer drug. It is further demanded to explore such a novel anti-cancer drug which is capable of inducing apoptosis and which is effective to cause apoptosis to effect even on such type of cancer cells insusceptible to induction of immediate death of cells by apoptosis, as long as they are treated by the known anti-cancer drug. It is therefore demanded now to provide such novel compounds which have an activity of inducing apoptosis effectively even on cancer cells of such type insusceptible to induction of apoptosis (immediate death of cells) when treated with the known anti-cancer drugs.

DISCLOSURE OF THE INVENTION

We, the present inventors, have now made our investigations with the intention of providing some novel compounds which have activities to induce apoptosis strongly on cancer cells and which are thus useful to treat therapeutically the cancer. In this connection, we have an expectation that such physiologically active substance capable of inducing the apoptosis even on the human pancreatic adenocarcinoma cell, AsPC-1 cell, can exhibit a usefully effective anti-cancer activity, seeing that the AsPC-1 cell cannot induce apoptosis by the treatment with the conventional anti-cancer drug. Thus, we have made investigations to detect novel compound(s) having an activity of inducing the apoptosis on the AsPC-1 cell out of the metabolic products of microorganisms. As a result, we have now found that when such a strain of microorganism belonging to genus Streptomyces which we have newly isolated from a soil sample and we have allotted a strain No. MK498-98F14 is incubated, said strain has produced in the resulting culture broth such a substance which is capable of inducing apoptosis on the AsPC-1 cells. Then, we have successfully isolated this substance having the apoptosis-inducing activity and have studied on the physico-chemical properties and physiological activities of said substance, to find out that this substance be a novel compound. Thus, we have designated this compound as "polyoxypeptin".

We have further found that a second substance capable of inducing apoptosis on the AsPC-1 cells was also produced and present in the culture broth of the MK498-98F14 strain above-mentioned. We have successfully isolated the second compound, too. Then, we have studied on the physico-chemical properties and physiological activities of the second substance to find out that the second substance be a novel compound. Further, we have succeeded in deciding the chemical structures of polyoxypeptin firstly obtained, as well as the second substance subsequently obtained. We have then designated the second substance as "deoxypolyoxypeptin". We further have confirmed that deoxypolyoxypeptin has an apoptosis-inducing activity. Further, we have recognized that polyoxypeptin and deoxypolyoxypeptin can be represented collectively by a general formula (I) as shown below. It has further been found that polyoxypeptin and deoxypolyoxypeptin can be reacted at the site of acidic group thereof with an inorganic base or an organic base to form a salt, for example, sodium salt, potassium salt and an alkylamine salt.

According to a first aspect of this invention, therefore, there is provided, as the novel physiologically active substance, polyoxypeptin or deoxypolyoxypeptin, which is a compound represented by the following general formula (I)

(I)

wherein R denotes a hydroxyl group for polyoxypeptin or R denotes a hydrogen atom for deoxypolyoxypeptin, or a pharmaceutically acceptable salt thereof.

Polyoxypeptin according to the first aspect of this invention is the compound represented by the following formula (Ia)

(Ia)

Deoxypolyoxypeptin according to the first aspect of this invention is the compound represented by the following formula (Ib)

(Ib)

Figure 1:
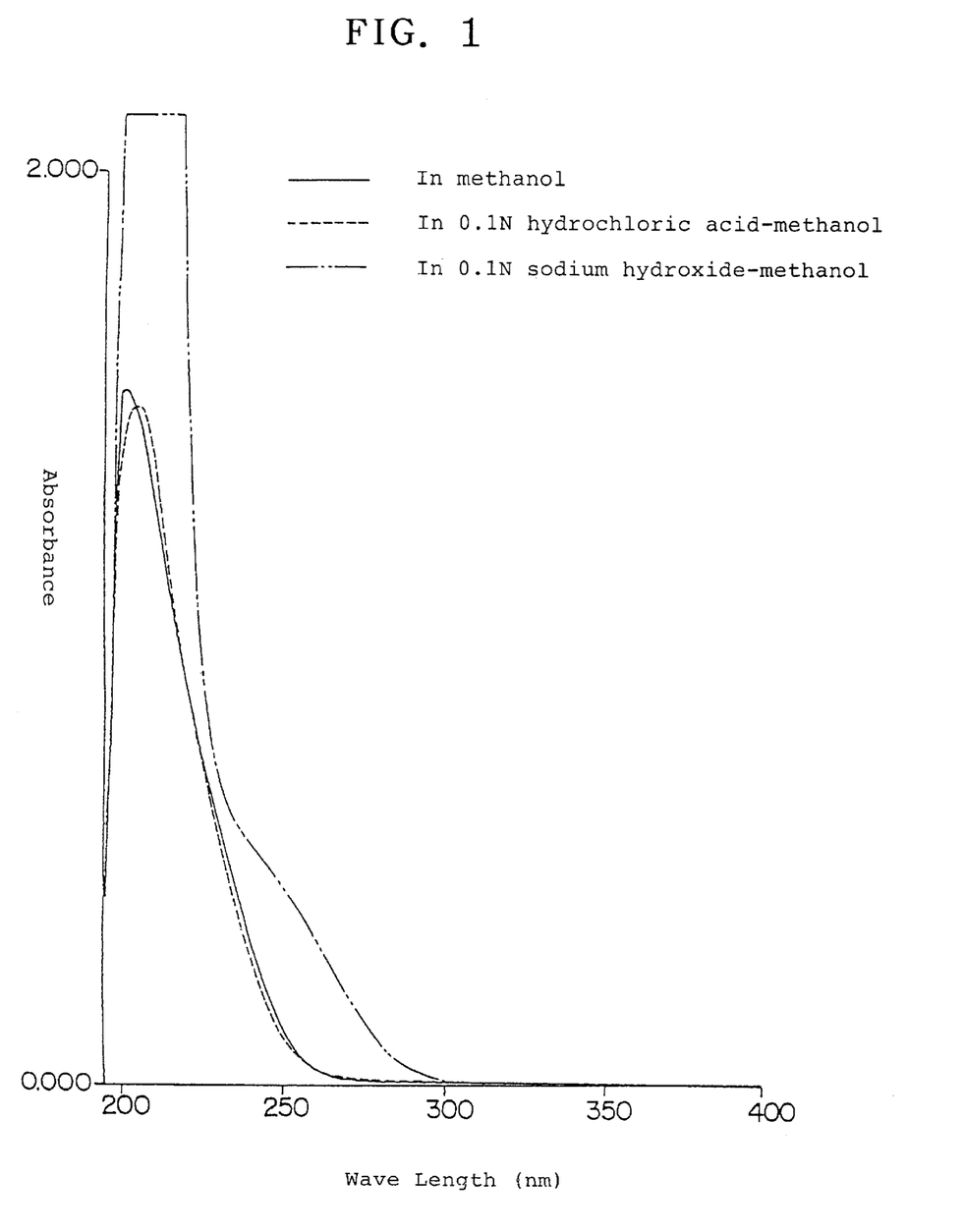
FIG. 1 shows an ultraviolet absorption spectrum of polyoxypeptin in a methanol solution (shown by a solid line); an ultraviolet absorption spectrum of polyoxypeptin in a 0. 1N hydrochloric acid- methanol solution (shown by a dotted line); and an ultraviolet absorption spectrum of polyoxypeptin in a 0.1N sodium hydroxide-methanol solution (shown by a broken line).
Figure 2:
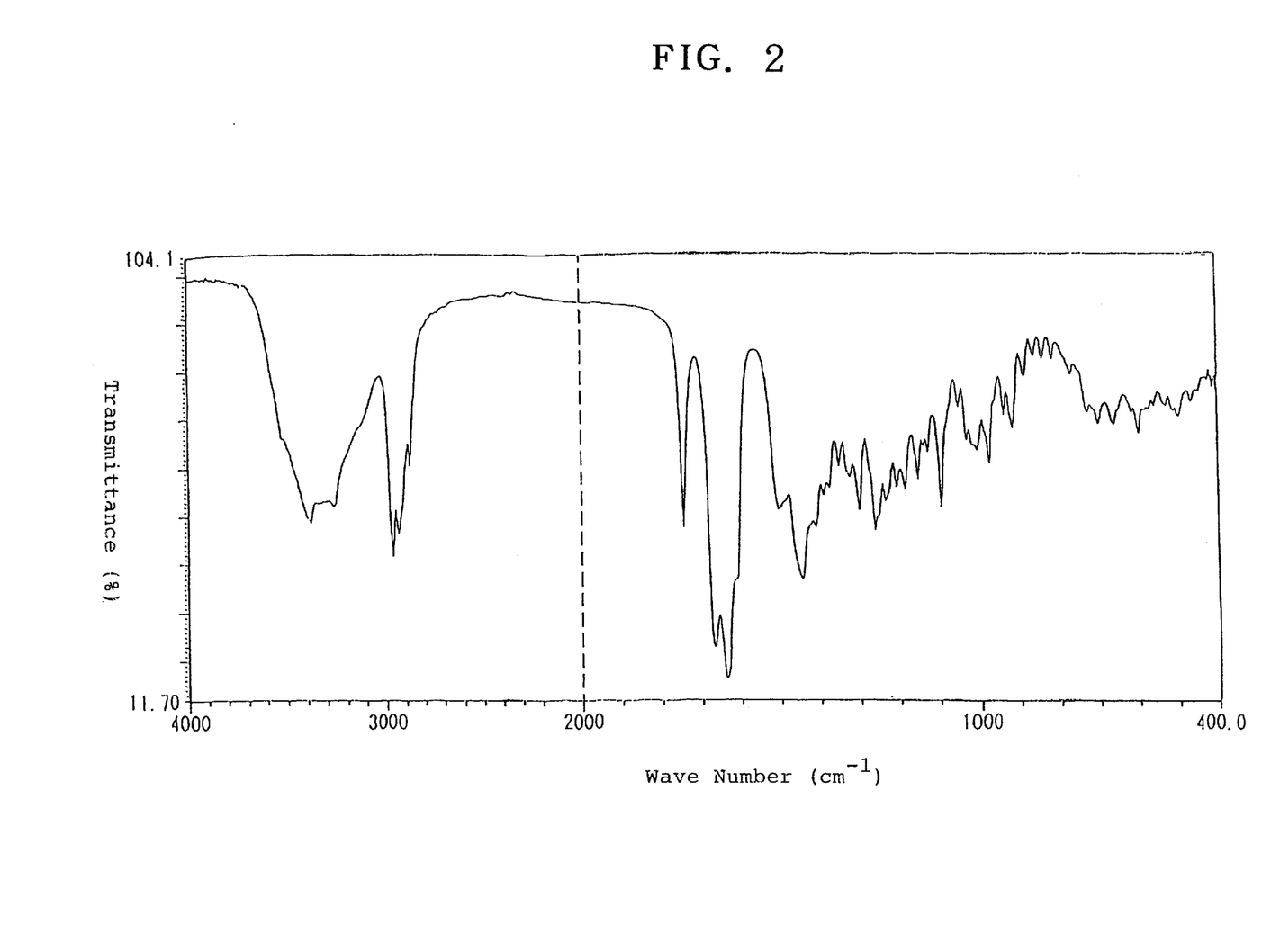
FIG. 2 shows an infrared absorption spectrum of polyoxypeptin as determined by KBr pellet method.
Figure 3:
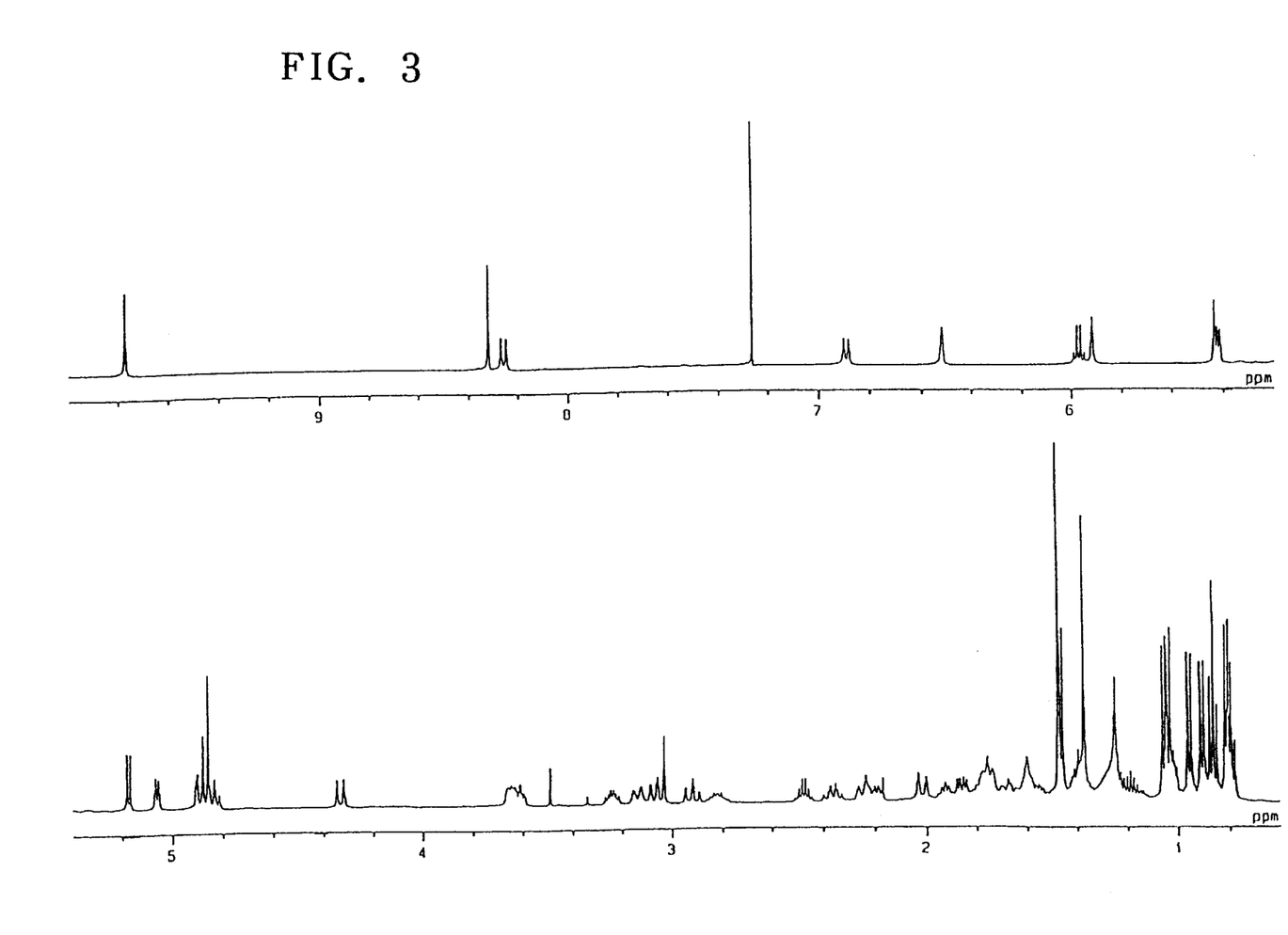
FIG. 3 shows a proton nuclear magnetic resonance spectrum (500 MHz) of polyoxypeptin as determined in a deutero-chloroform solution (internal standard: trimethylsilane).
Figure 4:
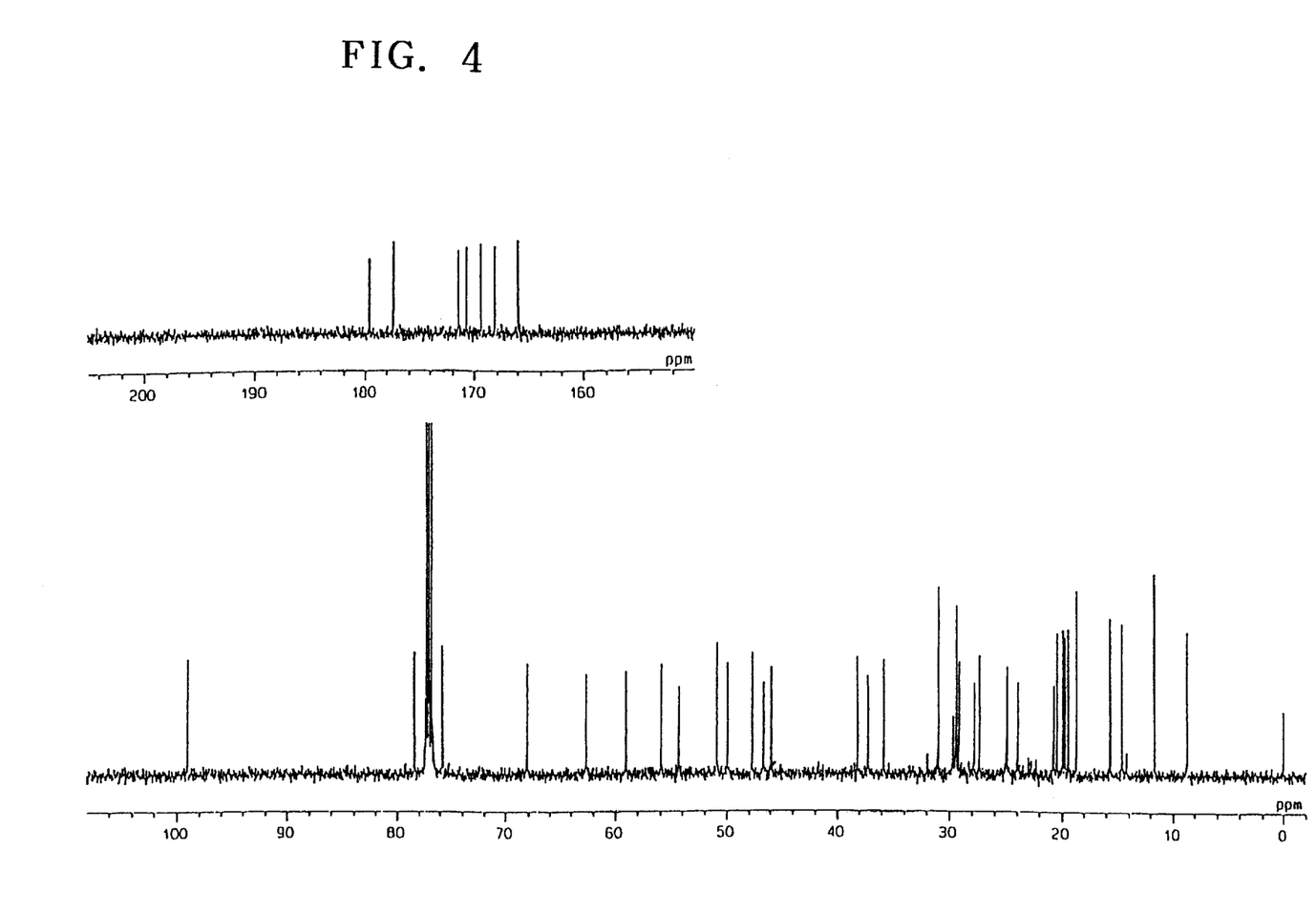
FIG. 4 shows a carbon 13 nuclear magnetic resonance spectrum (125 MHz) of polyoxypeptin as determined in a deutero-chloroform solution (internal standard: trimethylsilane).

Now, the physico-chemical properties of polyoxypeptin according to the first aspect of this invention are given below
(1) Appearance: Colorless crystals.
(2) Molecular formula: $C_{45}H_{76}N_8O_{15}$.
(3) High resolution FAB-MS spectrum (m/z): 991.5356 $(M+Na)^+$
(4) Melting point: 244~245° C.
(5) Specific optical rotation: $[\alpha]_D^{22}$ +162 (c 0.5, $CHCl_3$)
(6) Solubility: Soluble in methanol, ethanol, aqueous ethanol, chloroform, ethyl acetate, acetone, n-butanol, acetonitrile, toluene, dimethylsulfoxide; but hardly soluble in water.
(7) Rf value of TLC:
  (i) 0.56 (when determined on a thin layer of silica gel as developed with chloroform-methanol (20:1) as the developing solvent).
  (ii) 0.64 (when determined on a thin layer of silica gel as developed with toluene-acetone (1:1) as the developing solvent).
(8) Ultra-violet absorption spectrum: As shown in FIG. 1 of the accompanying drawings.
(9) Infrared absorption spectrum (potassium bromide pellet method): As shown in FIG. 2 of the accompanying drawings.
(10) Proton nuclear magnetic resonance spectrum (in deutero-chloroform, 500 MHz): As shown in FIG. 3 of the accompanying drawings.
(11) $^{13}$C-nuclear magnetic resonance spectrum (in deutero-chloroform,125 MHz): As shown in FIG. 4 of the accompanying drawings.

Then, the physico-chemical properties of deoxypolyoxypeptin according to the first aspect of this invention are given below in detail.
(1) Appearance: Colorless powder.
(2) Molecular formula: $C_{45}H_{76}N_8O_{14}$.
(3) FAB-MS spectrum (m/z): (pos.) 975 $(M+Na)^+$, (neg.) 951 $(M-H)^-$
(4) Melting point: 157~159° C.
(5) Specific optical rotation: $[\alpha]_D^{24}$ +124 (c 0.5, $CHCl_3$
(6) Solubility: Soluble in methanol, ethanol, aqueous ethanol, chloroform, ethyl acetate, acetone, butanol, acetonitrile, toluene, dimethylsulfoxide; but hardly soluble in water.
(7) Rf value of TLC:
  (i) 0.68 (when determined on a thin layer of silica gel as developed with chloroform-methanol (20:1) as the developing solvent).
  (ii) 0.82 (when determined on a thin layer of silica gel as developed with toluene-acetone (1:1) as the developing solvent).

Figure 5:
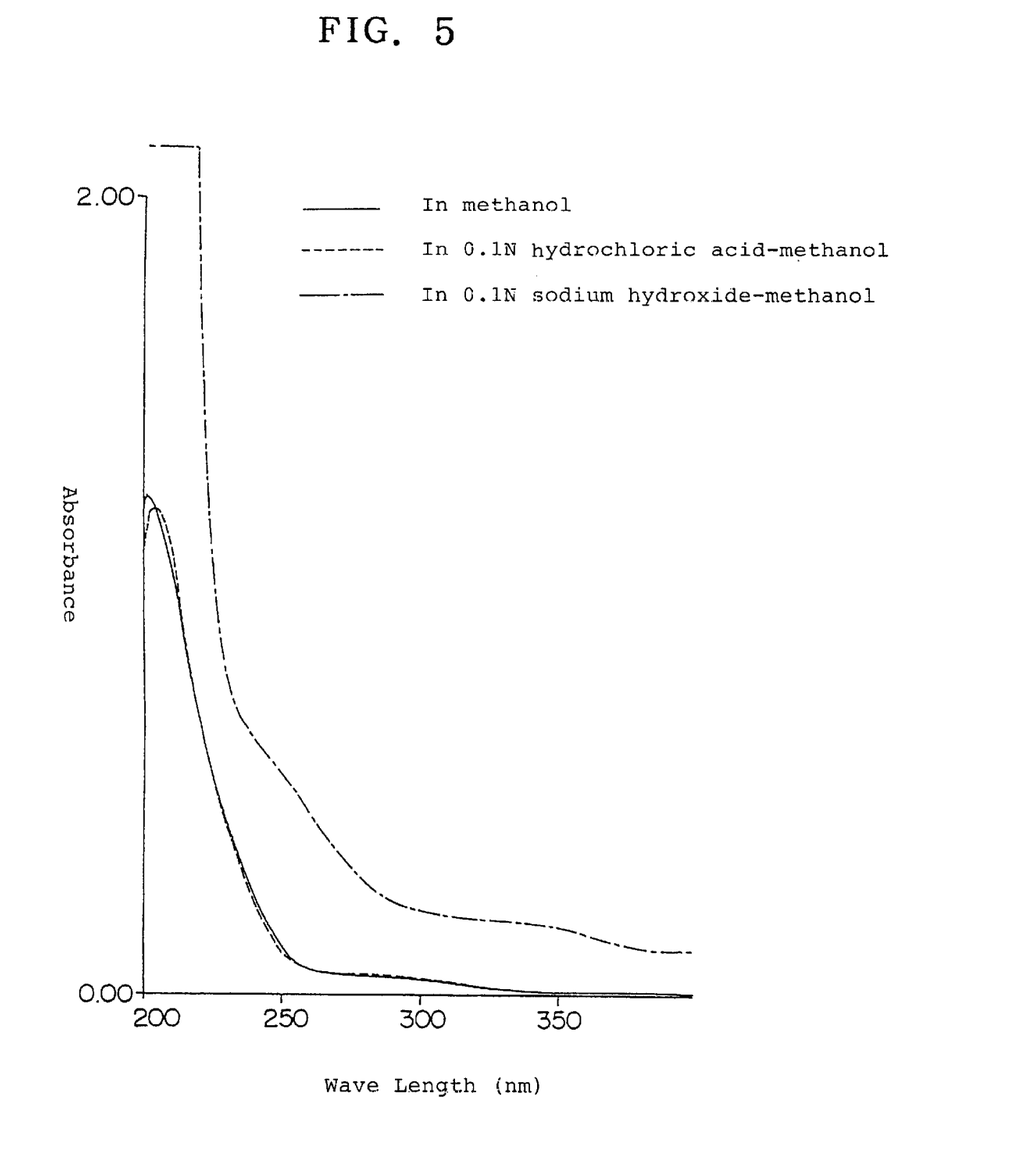
FIG. 5 shows an ultraviolet absorption spectrum of deoxypolyoxypeptin in a methanol solution (shown by a solid line); an ultraviolet absorption spectrum of deoxypolyoxypeptin in a 0.1N hydrochloric acid-methanol solution (shown by a dotted line); and an ultraviolet absorption spectrum of deoxypolyoxypeptin in a 0.1N sodium hydroxide-methanol solution (shown by a broken line).
Figure 6:
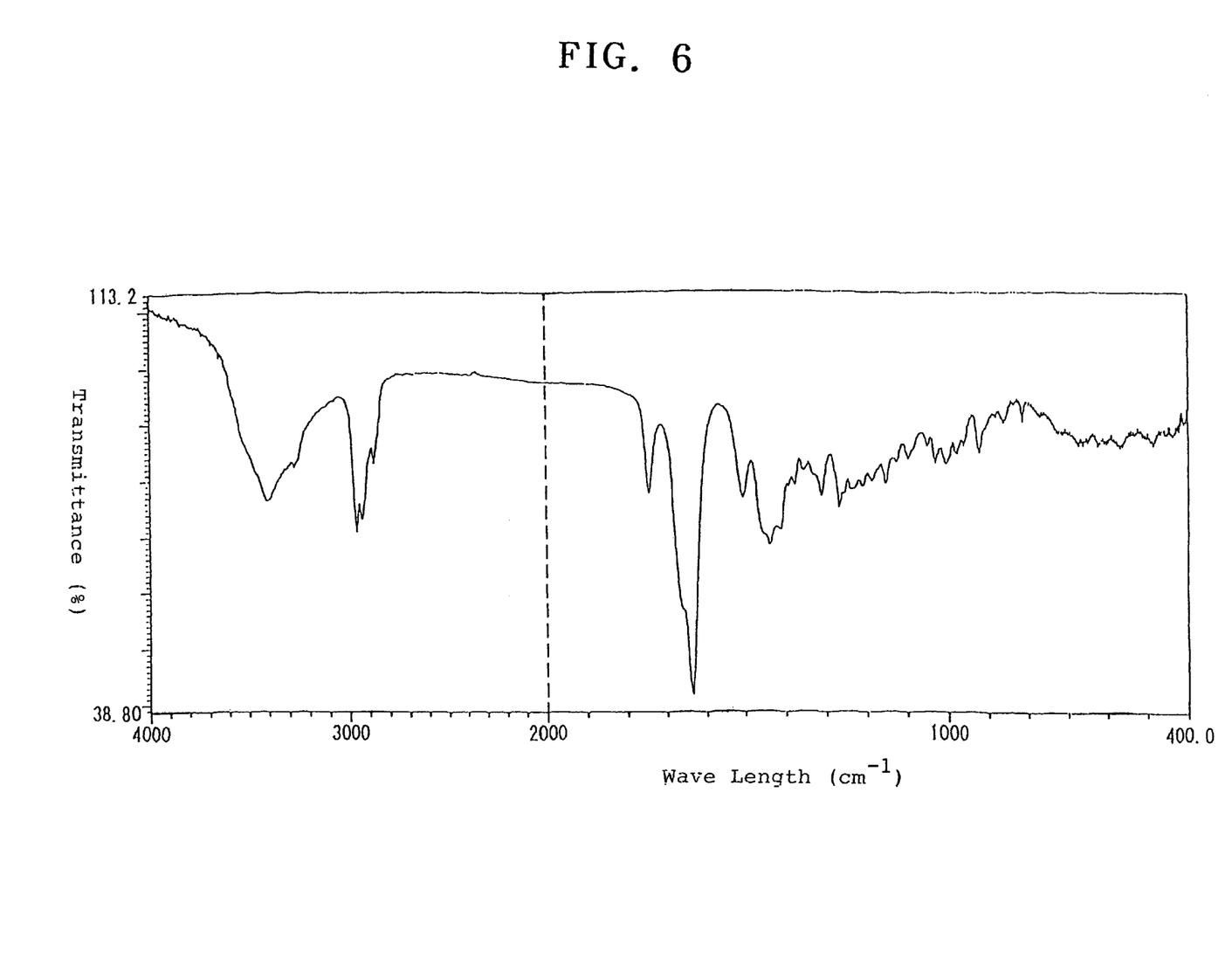
FIG. 6 shows an infrared absorption spectrum of deoxypolyoxypeptin as determined by KBr pellet method.
Figure 7:
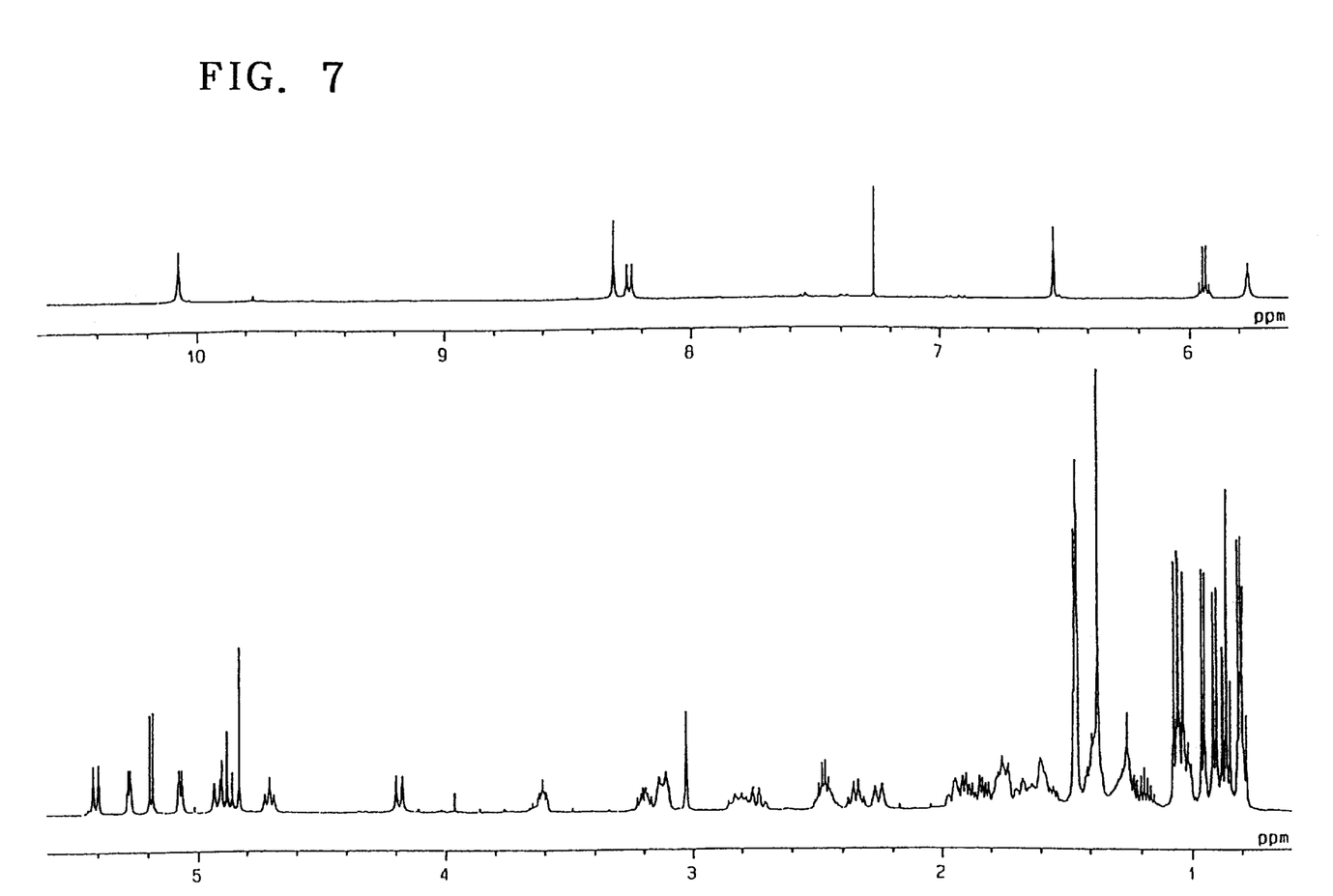
FIG. 7 shows a proton nuclear magnetic resonance spectrum (500 MHz) of deoxypolyoxypeptin as determined in a deuterochloroform solution (internal standard: trimethylsilane).
Figure 8:
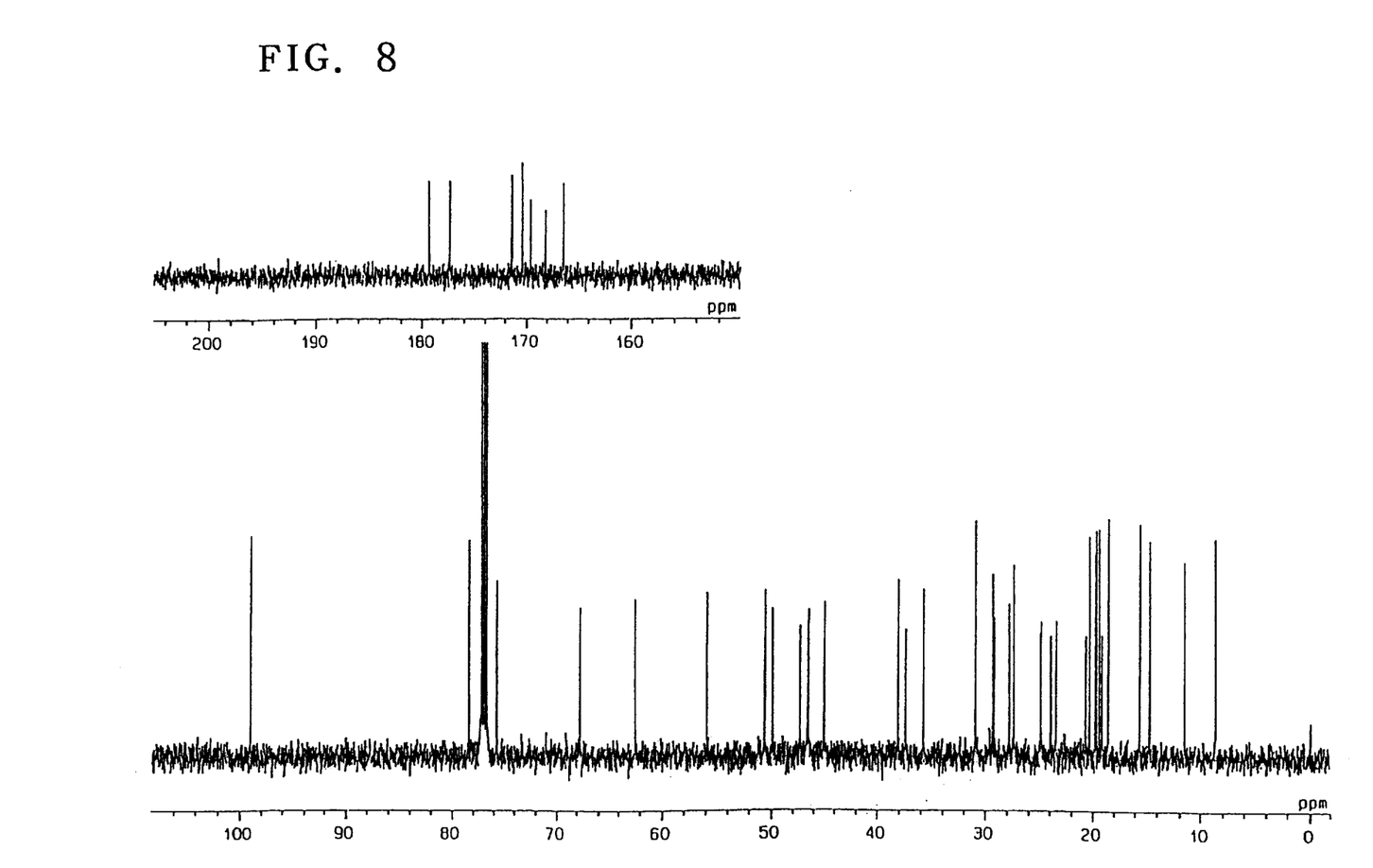
FIG. 8 shows a carbon 13 nuclear magnetic resonance spectrum (125 MHz) of deoxypolyoxypeptin as determined in a deuterochloroform solution (internal standard: trimethylsilane).

(8) Ultra-violet absorption spectrum: As shown in FIG. 5 of the accompanying drawings.
(9) Infrared absorption spectrum (potassium bromide pellet method): As shown in FIG. 6 of the accompanying drawings.
(10) Proton nuclear magnetic resonance spectrum (in deutero-chloroform, 500 MHz): As shown in FIG. 7 of the accompanying drawings.
(11) $^{13}$C-nuclear magnetic resonance spectrum (in deutero-chloroform, 125 MHz): As shown in FIG. 8 of the accompanying drawings.

Polyoxypeptin and deoxypolyoxypeptin according to the first aspect of this invention have the physiological activities given below.

(1) Estimation of the Apoptosis-inducing Activity on Human Pancreatic Cancer Cell, AsPC-1 Cell A cell suspension containing the AsPC-1 cells suspended in an RPMI 1640 culture medium containing 10% FBS was prepared, and 500 μl-portion each of the cell suspension was placed in a 24-well plastic plate in a proportion of $1\times10^5$ cells/well. The cell suspension was incubated at 37° C. under 5% $CO_2$ for 1 day. The AsPC-1 cells adhered onto the bottom surface of each well. Subsequently, polyoxypeptin or deoxypolyoxypeptin was added to the liquid culture medium present in each well so as to give the substance under test at a concentration of 3, 100 or 300 μg/ml. The cells were incubated for 24 hours.

Immediately after the incubation for 24 hours, the super-natant liquid (500 μl) of the culture medium remaining in each well was removed from each well of said plastic plate and discarded. Then, the plastic plate was washed twice with a PBS buffer solution (each 300 μl), and the washings were discharged. Thereafter, a trypsin-EDTA buffer solution (200 μl) was added to said plastic plate, and the incubation was effected at 37° C. under $CO_2$-free condition so as to peel the cells off from the plate. The cells so peeled were transferred to an Eppendorf tube. The Eppendorf tube was centrifuged (2400 rpm, 10 minutes) to deposit the cells down, and the super-natant was removed and discarded. A fresh amount of the liquid culture medium was added to the cells. An 80 μl-portion of the resulting cell suspension as formed in said tube was taken into another Eppendorf tube, to which were then added 20 μl of Trypan Blue staining solution (containing 4 mg/ml of Trypan Blue and 9 mg/ml of NaCl). The cell suspension was taken out from the resulting mixture by a pipette, and the cell suspension so pipetted was placed on a hemocytometer (made by Elma Co.). The cell sample was observed under a microscope of 100 magnifications. The number of the dead cells as blue-colored amongst the cells under observation, and the total number of whole cells under observation were counted.

The survival rate (%) of the cells was calculated by an equation of 100–[(number of dead cells÷ total number of tested cells)×100]. As a result, it was found that polyoxypeptin and deoxypolyoxypeptin each have an $IC_{50}$ value of 80 ng/ml, namely the value of such concentration of said compound at which the cell death by apoptosis can be induced at the rate of 50% of the total cell number of the AsPC-1 cells under test. It was also found that polyoxypeptin and deoxypolyoxypeptin each induced the apoptosis on the AsPC-1 cells in approximately 24 hours after the drug treatment.

(2) Estimation of the Activity Inhibitory to the Proliferation of Human Pancreatic Cancer Cell, AsPC-1 Cell A cell suspension of AsPC-1 cells suspended in an RPMI 1640 culture medium containing 10% FBS was prepared, and 100 μl-portion each of said cell suspension was placed in a 96-well plastic plate in a proportion of $3\times10^3$ cells/well. Each plate was then incubated at 37° C. under a 5% $CO_2$ for 1 day. Subsequently, polyoxypeptin or deoxypolyoxypeptin was added to the liquid culture medium present in each well at a concentration of 1, 3, 10, 30 or 100 ng/ml of said compound. Then the incubation of the cells was effected for 2 days. Then, the number of cells was counted by MTT assay method. As a result, it was found that the concentration each of polyoxypeptin and deoxypolyoxy -peptin at which the proliferation of AsPC-1 cells was inhibited by 50%, that is, $IC_{50}$ value, was amounting to 15 ng/ml.

(3) Estimation of the Cytocidal Activity Against Various Cancer Cells

Various cancer cells as shown in Table 1 below were incubated for 24 hours on such culture medium as shown in the table which contained polyoxypeptin or deoxypolyoxypeptin added at various concentrations. After staining with Trypan Blue, the number.of the dead cells was counted, and the concentration of polyoxypeptin or deoxypolyoxypeptin required to kill 50% of the total number of cells of the cancer cells under test, namely the value of $IC_{50}$, was calculated therefrom. Both polyoxypeptin and deoxypolyoxypeptin showed a same level of the $IC_{50}$ value. The $IC_{50}$ values calculated are shown in Table 1. It is found that the above-mentioned compounds so tested have the cyotocidal activities against various cancer cells shown in the following table.

TABLE 1

| Cancer cells | Culture medium | $IC_{50}$ (μg/ml) |
| --- | --- | --- |
| Human pancreatic adenocarcinoma cells AsPC-1 | A | 0.08 |
| Human pancreatic adenocarcinoma cells BxPC-3 | A | 0.03 |
| Human pancreatic adenocarcinoma cells PSN-1 | A | 0.01 |
| Human pancreatic adenocarcinoma cells Panc-1 | A | 0.05 |
| Human bibrosarcoma HT1080 | D | 0.02 |
| Human epithelioma A431 | C | 0.03 |
| Human T cell leukemia Jurkat | B | 0.05 |
| Human uterus body cancer HHUA | D | 0.05 |
| Rat fibroblast cell NRK | C | 0.18 |
| Rat fibroblast cell K-ras-NRK | C | 0.05 |
| Mouse fibroblast cell NIH3T3 | A | 0.05 |
| Mouse fibroblast cell K-ras-NIH3T3 | A | 0.10 |
| Mouse fibroblast cell A4 (cerbB2-NIH3T3) | A | 0.06 |
| Mouse fibroblast cell RSV-NIH3T3 (src-transformed NIH3T3) | A | 0.06 |
| Human promyeloleukemia HL-60 | A | 0.04 |
| Human chronic promyeloleukemia K562 | A | 0.02 |

Medium A: RPMI 1640 culture medium containing 10% FBS

Medium B: RPMI 1640 culture medium containing 10% immobile FBS

Medium C: DMEM culture medium containing 5% CS

Medium D: DMEM culture medium containing 10% FBS (4) Antibacterial Activity

Antibacterial spectra of polyoxypeptin and deoxypolyoxypeptin against various microorganisms were determined on Muller-Hinton agar medium by a serial dilution method on the basis of the standard method of Japan Society of Chemotherapy.

Polyoxypeptin and deoxypolyoxypeptin exhibited an antibacterial activity against a gram-positive bacterium, *Staphylococcus aureus*, at a minimum inhibitory concentration of 6.25~12.5 μg/ml. However, they did not exhibit any antibacterial activity against gram-negative bacteria such as *Escherichia coli*.

(5) Acute Toxicity

Polyoxypeptin of this invention, when administered once to mice(4 mice per group) by intravenous injection, exhibited an $LD_{50}$ value of 67.5 μg/mouse. Deoxypolyoxypeptin as administered similarly exhibited an $LD_{50}$ value of 125 μg/mouse.

Further, according to a second aspect of this invention, there is provided a process for the preparation of physiologically active substances, polyoxypeptin and/or deoxypolyoxypeptin, characterized in that the process comprises cultivating a polyoxypeptin- and deoxypolyoxypeptin-producing strain belonging to the genus Streptomyces, and recovering from the resulting culture polyoxypeptin or deoxypolyoxypeptin or both of them.

The polyoxypeptin- and deoxypolyoxypeptin-producing strain to be used in the process of this invention may be any one of any species, so far as it has an ability to produce polyoxypeptin and deoxypolyoxypeptin. Said strains can be chosen from a wide variety of microorganisms. Of those micro-organisms, there is exemplified, as one concrete example of preferred polyoxypeptin- and deoxypolyoxypeptin-producing strain, the strain belonging to Actinomycetes which was separated by the inventors of this invention in November, 1995 at Biseibutsu Kagaku Kenkyujo, from a soil sample collected at Mateyama, Shiragami-dake in A-omori Prefecture, Japan, and to which was allotted a strain number MK498-98F14.

The microbiological properties of MK498-98F14 strain are shown below.

1. Morphology

MK498-98F14 strain has branched substrate mycelia, from which aerial hyphae develop with formation of whirls. Chain of the matured spores is in the form of chain comprising 10 to 50 or more of ovoid spores, measuring about 0. 5~0.8×0.8~13 microns. The surface of the spores is spinny. None of the whirl, mycelial strand, sporangium and motile spore is observed.

2. Growth Characteristics on Various Culture Media

The standard given in each of the brackets [ ] for the description of color is according to "Color Harmony Manual" of Container Corporation of America.

(1) Sucrose-nitrate-agar Medium (cultured at 27° C.)

Aerial hyphae of white grayish white [2dc, Natural] are formed on the growth of pale yellow [1 ca, Pale Yellow]. No soluble pigment is observed.

(2) Glycerine-asparagine-agar Medium (ISP-medium 5, cultured at 27° C.)

Aerial hyphae of white in color are thinly formed on the growth of pale yellowish brown [3 ie, Camel] in color. Soluble pigment is tinged with brown.

(3) Starch-inorganic salt-agar Medium (ISP-medium 4, cultured at 27° C.)

Aerial hyphae of white bright gray [15 dc, Dawn Blue] in color are formed on the growth of dusty yellow [1 ½ gc, Dusty Yellow] in color. No soluble pigment is observed.

(4) Tyrosine-agar Medium (ISP-medium 7, cultured at 27° C.)

Aerial hyphae of bright gray [f] in color are formed on the growth of pale yellow [1 ca, Pale Yellow] to yellowish gray [2 ec, Biscuit] in color. No soluble pigment is observed.

(5) Yeast-malt-agar Medium (ISP-medium 2, cultured at 27° C.)

Aerial hyphae of bright gray [15 dc, Dawn Blue] to pale blue [13 ½ ea, Lt Sky Blue] in color are formed on the growth of pale yellowish brown [2 gc, Bamboo] in color. No soluble pigment is observed.

(6) Oatmeal agar Medium (ISP-medium 3, cultured at 27° C.)

Aerial hyphae of white to bright gray [15 dc, Dawn Blue] are formed on the growth of pale yellow [1 ca, Pale Yellow] in color. No soluble pigment is observed.

3. Physiological Properties (1) Temperature Range for the Growing

MK498-98F14 strain was incubated in a glucose-asparagine-agar medium (containing 1.0% glucose, 0.05% asparagine, 0.05% dipotassium hydrogen phosphate and 2.4% string agar, pH 7.0) at different temperatures of 10° C., 20° C., 24° C., 27° C., 30° C., 37° C. and 50° C. each. The result showed that the MK498-98F14 strain could grow at any of the temperatures except 10, 37° C. and 50° C. The optimum growth temperature seems to be in the vicinity of 30° C.

(2) Hydrolysis of Starch (starch-inorganic salt-agar medium, ISP- medium 4 and starch-agar medium, cultured at 27° C. for each medium)

No hydrolysis of starch was observed for incubation of 21 days in each medium.

(3) Formation of Melanin Pigment (Trypton-yeast-broth, ISP-medium 1; peptone-yeast-iron agar medium, ISP-medium 6; tyrosine-agar medium, ISP-medium 7, cultured at 27° C. for each medium)

The formation of melanin was negative in all the media used.

(4) Utilization of Carbon Sources (Pridham-Gottlieb agar medium, ISP-medium 9, cultured at 27° C.)

D-glucose, D-fructose and rhamnose are utilizable for the growth, but the utilization of L-arabinose and inositol is indefinite, and xylose, sucrose, raffinose and D-mannitol are not utilizable.

(5) Reduction of Nitrate (aqueous peptone solution containing 0.1% potassium nitrate, ISP-medium 8, cultured at 27° C.)

The reduction is positive.

Summarizing the above-mentioned properties, MK498-98F14 strain is characterized in that it has branched substrate, from which aerial hyphae develop with formation of whirls, that the chain of matured spores comprises 10 to 50 or more of spores of oval shape, the surface of which surface is spinny, that on various culture media, aerial hyphae of white to grayish white in color are formed on the growth of pale yellow to pale yellowish brown in color, that soluble pigment tinged faint brown is observed on ISP-medium 5, but no soluble pigment is observed on any other media, that the optimum growth temperature is in the vicinity of 30° C., and that the formation of melannoid pigment is negative. In addition, 2,6-diaminopimelic acid contained in the cell wall is of the LL-form. Menaquinone as the cell component contains $MK-9(H_4)$ and $MK-9(H_6)$.

In view of these properties, it is supposed that MK498-98F14 strain belongs to the genus Streptomyces. When searching the analogous known species with reference to the properties of this strain, there may be mentioned *Streptomyces viridodiastatics* (Literature: International Journal of Systematic Bacteriology, 19, 500 (1969)), *Streptomyces ambofaciens* (Literature: International Journal of Systematic Bacteriology, 18, 290 (1968)), *Streptomyces rubiginosus* (Literature: International Journal of Syster aLatic Bacteriology, 18, 374(1968)) and *Streptomyces albogriseolus* (Literature: International Journal of Systematic Bacteriology, 18, 289 (1968)). Thus, we intend to actually study and examine by MK498-98F14 strain in direct comparison with the above-mentioned four strains which have been preserved in our Research Laboratory. At this time, MK498-98F14 strain is designated as Streptomyces sp. MK498-98F14.

The strain MK498-98F14 was applied to be deposited in the Japanese depository "National Institute of Bioscinence and Human-Technology, Agency of Industrial Science & Technology, which locates at Tsukuba-City, Ibaraki Prefecture, Japan, and said strain has been deposited as of Apr. 18, 1997 under FERM P-16200. Further, the strain MK498-98F14 has been deposited since May 25, 1998 under the deposit number of FERM BP-6374 in terms of Budapest Treaty.

In practicing the process according to the second aspect of this invention, a polyoxypeptin- and deoxypolyoxypeptin producing strain belonging to the genus Streptomyces, particularly MK498-98F14 strain (deposited under FERM BP-6374), is inoculated to a nutrient culture medium and incubated therein. The nutrient culture medium used here may be one containing carbon source and nitrogen source as the nutrients which are assimilable with the said strain.

As the nutrient sources, there may be used such those which are ordinarily used as the nutrient sources of microorganisms, and which are for example, assimilable nutrient sources such as carbon sources, nitrogen sources, norganic salts and the like. For example, there may be used such carbon sources which are carbohydrates, including glucose, maltose, molasses, dextrin, glycerin, starch and the like, as well as oils and fats, including soybean oil, peanut oil and the like. As nitrogen sources, there may be used peptone, meat extract, cotton seed meal, soybean powder, yeast extract, casein, corn steep liquor, NZ-amine, ammonium sulfate, ammonium nitrate, ammonium chloride and the like. Further, inorganic salts may be added to the culture medium, such as dipotassium hydrogen phosphate, sodium phosphate, sodium chloride, calcium carbonate, magnesium sulfate, manganese chloride and the like. If necessary, trace amount of metals, for example, cobalt, iron, etc. may also be added. In addition, any other known nutrient source may be used, as long as the strain used is capable of utilizing such nutrient source for the production of polyoxypeptin and deoxypolyoxypeptin.

The proportions of the above-mentioned nutrient sources to be incorporated in the culture medium are not particularly limited, but may vary over a wide range. The optimum compositions and proportions of the nutrient sources to be incorporated can easily be determined through simple small-scale experiments by those skilled in the art, depending upon the nature of polyoxypeptin- and deoxypolyoxypeptin-producing strain to be used. The nutrient culture medium comprising the above-mentioned nutrients may be sterilized before the cultivation of the strain is conducted. It is advantageous to adjust the pH of the culture medium to a range f 7~8, particularly to a range of 7.0~7.5 before or after the sterilization of the culture medium.

The cultivation of the polyoxypeptin- and deoxypolyoxypeptin-producing strain in such a nutrient culture medium may be effected in accordance with any conventional method ordinarily used in the production of antibiotics by the genus Actinomyces. Preferably, the cultivation may be carried out under aerobic conditions, usually under stirring and/or under aeration. As the cultivation method, there may be usable any of stationary cultivation, shaking cultivation and submerged cultivation under aeration and stirring. The submerged cultivation is suitable for the purpose of large scale production of polyoxypeptin and/or deoxypolyoxypeptin.

The available cultivation temperature is not specifically limited, so far as it is within the range of temperature at which the growth of the polyoxypeptin- and deoxypolyoxypeptin-producing strain is substantially not prevented and thus polyoxypeptin and deoxypolyoxypeptin can be produced. The cultivation temperature may suitably be chosen depending upon the nature of the strain used, and a particularly preferred cultivation temperature may be in the range of 25~30° C. The cultivation may usually be continued until sufficient amount of polyoxypeptin and/or deoxypolyoxypeptin has been accumulated in the culture. The cultivation period of time may vary depending upon the composition of the culture medium, cultivation temperature, the antibiotic-producing strain as used, and so on. Usually, the cultivation for 72~150 hours may give the target antibiotics.

The accumulated amount of the novel substances, polyoxyvpeptin and deoxypolyoxypeptin during the cultivation may be quantitatively determined by using Staphylococcus aureus Smith in accordance with a cup-plate method which is conventionally used for quantitative determination of antibiotics.

Polyoxypeptin and/or deoxypolyoxypeptin thus accumulated in the resultant culture is then recovered therefrom. In order to recover the intended substances, the culture broth, after the above-mentioned cultivation, is subjected to a known process of separating the microbial cells, such as filtration, centrifugation, etc. to separate the mycelial cells, when necessary. Thereafter, the resulting broth filtrate or the mycelial cells may be treated by a solvent extraction method with an organic solvent, particularly ethyl acetate, or by a chromatography with utilizing adsorption or ion-exchange, or by a gel filtration or by counter current distribution, singly or in combination, whereby the target substances can be isolated and purified. As a carrier having the adsorbability or ion-exchangeability for use in such chromatography as above, there may be employed silica gel, porous polystyrene-divinylbenzene resin or various ion-exchange resins. The mycelial cells as separated or the disrupted mycelial cells may be treated by a solvent extraction method with a suitable organic solvent for discharging the intercellular components, so that the intended polyoxypeptin and/or deoxypolyoxypeptin can be extracted out from the cells. The target substances so extracted out may then be isolated and purified in the same manner as above. In this way, the novel substances, polyoxypeptin and/or deoxypolyoxypeptin having the above-mentioned characteristics can be obtained.

Further, according to a third aspect of this invention, there is provided a pharmaceutical composition comprising as an active ingredient the polyoxypeptin or deoxypolyoxypeptin or a pharmaceutically acceptable salt thereof, in combination with a pharmaceutically acceptable carrier for the active ingredient.

The pharmaceutical composition according to the third aspect of this invention may be such an anti-cancer or anti-tumor drug composition which is in the form of a mixture comprising as the active ingredient polyoxypeptin or deoxypolyoxypeptin or a pharmaceutically acceptable salt thereof as uniformly blended with a conventional, solid or liquid and pharmaceutically acceptable carrier, for example, ethanol or starch.

Polyoxypeptin or deoxypolyoxypeptin or a salt thereof to be used as the active ingredient in the pharmaceutical composition according to the third aspect of this invention may be administered by orally or by parenterally, for instance by intravenous or intramuscular injection, etc. It may also be administered percutaneously.

For oral administration, the pharmaceutical composition according to the third aspect of this invention may be prepared in the form of various preparations such as tablets, buccal tablets, troaches, capsules, suspensions, syrups and the like, by mixing polyoxypeptin or deoxypolyoxypeptin or a salt thereof as the active ingredient with a conventional solid or liquid carrier or carriers.

The proportion of the compound of formula (I) above as the active ingredient present in the pharmaceutical composition according to the third aspect of this invention may vary depending upon the form of preparations. A convenient proportion of the active ingredient may be in the range of about 2~60% based on the weight of an administration unit of the composition.

When the composition of the third aspect of this invention is to be prepared in the form of injection preparations, preferred form of the injectable preparations are, for example, a sterile aqueous dispersion or a sterile lyophilized preparation. As a liquid carrier used here, there may preferably be exemplified water, aqueous ethanol, glycerol, propylene glycol, vegetable oils and the like. When the composition of the third aspect of this invention is to be prepared in the form of dispersion preparations, the dispersed state of the ingredient active compound in the dispersion preparation can be kept well by giving the active ingredient compound a desired particle size, and by adding a viscosity-regulating agent such as lecithin. Further, it is preferred, in most cases, that the injection preparation contain an isotonic agent such as sugar or sodium chloride.

The administration dosage of polyoxypeptin or deoxypolyoxypeptin or a salt thereof used in the pharmaceutical composition of this invention may vary depending upon the nature of diseases to be treated, the purpose of the treatment and the degree of disease symptom. However, the dosage may usually be 0.2~10 mg per day for adult, which may be administered once or several times. An optimal dose may be decided by those skilled in the art by conducting suitable preliminary tests.

Further, according to a fourth aspect of this invention, there is provided a use of polyoxypeptin or deoxypolyoxypeptin or a pharmaceutically acceptable salt thereof for the preparation of the pharmaceutical composition.

Furthermore, according to a fifth aspect of this invention, there is provided, as a novel microorganism, Streptomyces sp. MK489-98F14 strain having a characteristic nature capable of producing polyoxypeptin and deoxypolyoxypeptin above-mentioned.

BEST MODE FOR CARRYING OUT THE INVENTION

This invention is now illustrated further in detail by the following Example, but is not limited thereto.

EXAMPLE 1

Production of physiologically active substances, polyoxypeptin and deoxypolyoxypeptin One hundred (100) ml-portion of a liquid culture medium comprising 1.0% glucose, 1.0% potato starch, 1.0% glycerol, 0.5% polypepton, 0.5% meat extract, 0.5% sodium chloride and 0.32% calcium carbonate(adjusted to pH 7.4) was poured into each of 500 ml-capacity Erlenmeyer flasks which each were 10 containing 1 drop of a silicone antifoaming agent. The flasks were then sterilized at 120° C. under a pressures of 2 atm. for 20 minutes. To the sterilized culture medium, was inoculated the MK498-98F14 strain (FERM BP-6374)of the genus Streptomyces from a slant culture thereof. The shake cultivation of said strain was effected at 27° C. at 180 r.p.m. under an aerobic condition. Thus, a culture broth was obtained.

Four hundred liters of the culture broth so obtained from the cultivation for 96 hours were extracted once with the same volume of ethyl acetate without removal of the mycelia cells from the broth. The culture broth so once extracted was again extracted twice with a half volume of ethyl acetate. The resulting organic phase (the ethyl acetate extracts) was dried under a reduced pressure to yield 1.2 g of an oily substance.

The oily substance obtained was dissolved in a small volume of chloroform, and the resulting solution was adsorbed on a small amount of silica gel 60 (a product of Merck Co.), followed by drying under a reduced pressure. The silica gel so dried was then placed on the top of a column of 60 g of silica gel 60 which had been equilibrated with hexane. Then, the silica gel column was eluted successively with mixtures of hexane-ethyl acetate in various ratios (1:0, 5:1, 4:1, 3:1, 2:1, 1:1, 1:3, 1:5), while the eluate was collected in 500 ml-fractions. Further, the silica gel column was then eluted with mixtures of chloroform-methanol in various ratios (100:0, 100:2, 100:4, 100:6, 100:8, 100:20) successively, while the eluate was collected in 500 ml-fractions.

Of the eluate fractions so collected, the active fractions which had been collected upon the elution with the 1:3 mixture of hexane-ethyl acetate and with the 1:5 mixture of hexane-ethyl acetate, were combined and dried under a reduced pressure. The resulting solid obtained here (400 mg) was washed with a small volume of cold methanol and then dried under a reduced pressure. Thus, 330 mg of polyoxypeptin were obtained in the form of colorless crystals. Melting point: 244~245° C.

Further, the active fractions which had been collected upon the elution with the 100:4 mixture, 100:6 mixture and 100:8 mixture of chloroform-methanol above, were combined together and dried under a reduced pressure. The resulting solid obtained (360 mg) was again placed on the top of a column of silica gel 60 (18 g). This silica gal column was eluted successively with mixtures of toluene-acetone in various ratios (100:0, 20:1, 10:1, 5:1, 4:1, 3:1, 2:1, 1:1, 1:5, 1:10, 1:30), while the eluate was collected in 150 ml-fraction each. Of these eluate fractions, the active fraction which was obtained upon eluting with the mixture of toluene-acetone (10:1)was dried under a reduced pressure. Thus, 15 mg of deoxypolyoxypeptin was obtained as colorless powder. Melting point: 157~159° C.

INDUSTRIAL APPLICABILITY

As explained hereinbefore, polyoxypeptin and deoxypolyoxypeptin as provided by this invention have an activity of inducing the apoptosis even on such human pancreatic adenocarcinoma cells which are apoptosis-resistant, that is, on AsPC-1 cell, and they have also an activity of inducing apoptosis on other human solid cancer cells. Accordingly, polyoxypeptin and deoxypolyoxypeptin are useful as an anti-cancer agent.

What is claimed is:

1. Polyoxypeptin or deoxypolyoxypeptin which is a compound represented by the following general formula (I)

(I)

wherein R denotes a hydroxyl group for polyoxypeptin or R denotes a hydrogen atom for deoxypolyoxypeptin, or a pharmaceutically acceptable salt thereof.

2. A compound according to claim 1 which is a compound of general formula (I) where R is a hydroxyl group, namely polyoxypeptin represented by the following formula (Ia)

(Ia)

3. A compound according to claim 1 which is a compound of general formula (I) where R is a hydrogen atom, namely deoxypolyoxypeptin represented by the following formula (Ib)

(Ib)

4. A process for the production of polyoxypeptin and/or deoxypolyoxypeptin, characterized in that the process comprises cultivating a polyoxypeptin- and deoxypolyoxy peptin-producing strain belonging to the genus Streptomyces, and recovering from the resulting culture polyoxypeptin or deoxypolyoxypeptin or both of them.

5. A process according to claim 4 wherein as the polyoxypeptin- or deoxypolyoxypeptin-producing strain is used Streptomyces sp. MK498-98f14 strain which has been deposited in National Institute of Biascience and Human-Technology, Agency of Industrial Science & Technology, under the deposit number FERM BP-6374.

6. A pharmaceutical composition comprising as an active ingredient polyoxypeptin or deoxypolyoxypeptin or a pharmaceutically acceptable salt thereof, in admixture with a pharmaceutically acceptable carrier for the active ingredient.

7. A composition according to claim 6 wherein the pharmaceutical composition is for treatment of a cancerous condition selected from the group consisting of pancreatic adenocarcinoma, bibrosarcoma, epithelioma, T cell leukemia, uterus body cancer, fibroblast cells, promyel oleukemia or chronic promyeloleukemia.

8. A Streptomyces sp. MK498-98F14 strain which is identifiable by the strain as deposited under the access number FERM BP-6374 in the National Institute of Bioscience and Human Technology, Agency of Industrial Science & Technology, in accordance with the terms of the Budapest Treaty.

* * * * *